(12) United States Patent
Miesel et al.

(10) Patent No.: US 8,323,244 B2
(45) Date of Patent: Dec. 4, 2012

(54) CATHETER MALFUNCTION DETERMINATIONS USING PHYSIOLOGIC PRESSURE

(75) Inventors: Keith A. Miesel, St. Paul, MN (US); Robert J. Coffey, Thousand Oaks, CA (US)

(73) Assignee: Medtronic, Inc., Minneapolis, MN (US)

( * ) Notice: Subject to any disclaimer, the term of this patent is extended or adjusted under 35 U.S.C. 154(b) by 1194 days.

(21) Appl. No.: 11/731,356

(22) Filed: Mar. 30, 2007

(65) Prior Publication Data

US 2008/0243074 A1    Oct. 2, 2008

(51) Int. Cl.
*A61M 5/00* (2006.01)
*A61B 5/08* (2006.01)
*A61B 5/02* (2006.01)
*A61M 31/00* (2006.01)

(52) U.S. Cl. ........ 604/111; 600/485; 600/486; 600/488; 604/93.01

(58) Field of Classification Search .......... 600/485–486, 600/488; 604/93.01
See application file for complete search history.

(56) References Cited

U.S. PATENT DOCUMENTS

| | | |
|---|---|---|
| 3,882,443 A | 5/1975 | Mortia |
| 4,373,527 A | 2/1983 | Fischell |
| 4,388,833 A | 6/1983 | Kuwayama |
| 4,530,696 A * | 7/1985 | Bisera et al. ................. 604/253 |
| 4,534,756 A | 8/1985 | Nelson |
| 4,551,133 A | 11/1985 | Zegers de Beyl |
| 4,619,653 A | 10/1986 | Fischell |
| 4,710,163 A | 12/1987 | Butterfield |
| 4,714,462 A | 12/1987 | DiDomenico |
| 4,784,645 A | 11/1988 | Fischell |
| 4,979,940 A | 12/1990 | Bobo, Jr. |
| 5,006,997 A | 4/1991 | Reich |
| 5,024,668 A * | 6/1991 | Peters et al. ................. 606/194 |
| 5,040,536 A * | 8/1991 | Riff ................................. 607/23 |
| 5,059,171 A | 10/1991 | Bridge |

(Continued)

FOREIGN PATENT DOCUMENTS

EP    0 248 632 A2    12/1987

(Continued)

OTHER PUBLICATIONS

Geipel et al., "Design of an implantable active microport system for patient specific drug release", Proceedings of the 24th IASTED International Multi-conference on Biomedical Engineering (The International Association of Science and Technology for Development), Feb. 15-17, 2006, Innsbruck, Austria; pp. 161-166.

"The SynchroMed Pump" datasheet, [online]. Medtronic, Inc., Minneapolis, MN, Version b3.01, [retrieved on Oct. 19, 2007]. Retrieved from the Internet:<URL: http://www.medtronic.com/neuro/paintherapies/pain_treatment_ladder/drug_infusion/pumps_pump_sel/synchromed_pumps.html>; 4 pgs.

(Continued)

*Primary Examiner* — Nicholas Lucchesi
*Assistant Examiner* — Ian Holloway
(74) *Attorney, Agent, or Firm* — Mueting Raasch & Gebhardt PA (57) ABSTRACT

Methods and systems for determining whether an implanted catheter used to deliver fluids to a selected internal delivery site is malfunctioning. The malfunctions may include that the infusion section of the catheter is not located at or has migrated away from the selected internal delivery site, is leaking, is blocked, etc. The determination is made by analyzing the pressure modulation of fluid within the catheter and determining whether the pressure of the fluid in the catheter is modulated by physiologic pressure changes experienced at the selected internal delivery site. The physiologic pressure modulations at the selected internal delivery site may be caused by, e.g., cardiac activity, respiration, changes in patient's posture, etc.

35 Claims, 4 Drawing Sheets

U.S. PATENT DOCUMENTS

| | | |
|---|---|---|
| 5,078,682 A | 1/1992 | Miki |
| 5,087,245 A | 2/1992 | Doan |
| 5,096,385 A | 3/1992 | Georgi |
| 5,116,203 A | 5/1992 | Natwick |
| 5,158,547 A | 10/1992 | Doan et al. |
| 5,176,631 A | 1/1993 | Koenig |
| 5,190,522 A | 3/1993 | Wojcicki |
| 5,205,819 A | 4/1993 | Ross |
| 5,207,666 A | 5/1993 | Idriss |
| 5,276,610 A | 1/1994 | Maeda |
| 5,279,544 A | 1/1994 | Gross |
| 5,290,231 A | 3/1994 | Marcadis |
| 5,328,460 A | 7/1994 | Lord |
| 5,336,181 A | 8/1994 | Nakao |
| 5,342,298 A | 8/1994 | Michaels |
| 5,356,378 A | 10/1994 | Doan |
| 5,496,273 A | 3/1996 | Pastrone |
| 5,501,665 A | 3/1996 | Jhuboo |
| 5,535,752 A | 7/1996 | Halperin |
| 5,605,545 A | 2/1997 | Nowosielski |
| 5,609,576 A | 3/1997 | Voss |
| 5,669,877 A | 9/1997 | Blomquist |
| 5,695,473 A | 12/1997 | Olsen |
| 5,800,387 A | 9/1998 | Duffy |
| 5,827,223 A | 10/1998 | Butterfield |
| 5,853,386 A | 12/1998 | Davis |
| 5,893,838 A | 4/1999 | Daoud |
| 5,899,873 A | 5/1999 | Jones |
| 5,906,589 A | 5/1999 | Gordon |
| 5,928,195 A | 7/1999 | Malamud |
| 5,935,106 A | 8/1999 | Olsen |
| 6,152,898 A | 11/2000 | Olsen |
| 6,203,523 B1 | 3/2001 | Haller |
| 6,213,972 B1 | 4/2001 | Butterfield |
| 6,241,704 B1 | 6/2001 | Peterson |
| 6,358,225 B1 | 3/2002 | Butterfield |
| 6,394,986 B1 | 5/2002 | Millar |
| 6,423,029 B1 | 7/2002 | Elsberry |
| 6,423,035 B1 | 7/2002 | Das |
| 6,458,102 B1 | 10/2002 | Mann |
| 6,464,687 B1 | 10/2002 | Ishikawa |
| 6,485,465 B2 | 11/2002 | Moberg |
| 6,551,290 B1 | 4/2003 | Elsberry |
| 6,609,071 B2 | 8/2003 | Shapiro |
| 6,620,151 B2 | 9/2003 | Blischak |
| 6,648,821 B2 | 11/2003 | Lebel |
| 6,716,193 B1 | 4/2004 | Neftel |
| 6,740,059 B2 | 5/2004 | Flaherty |
| 6,742,999 B1 | 6/2004 | Nusser |
| 6,966,325 B2 | 11/2005 | Erickson |
| 7,022,116 B2 | 4/2006 | Morris |
| 7,054,782 B2 | 5/2006 | Hartlaub |
| 7,092,797 B2 | 8/2006 | Gaines |
| 7,104,763 B2 | 9/2006 | Bouton |
| 7,118,565 B2 | 10/2006 | Abboud |
| 7,255,680 B1 | 8/2007 | Gharib |
| 7,255,683 B2 | 8/2007 | Vanderveen |
| 7,291,126 B2 | 11/2007 | Shekalim |
| 7,311,693 B2 | 12/2007 | Shekalim |
| 7,320,676 B2 | 1/2008 | Miesel |
| 7,338,464 B2 | 3/2008 | Blischak |
| 7,437,644 B2 | 10/2008 | Ginggen |
| 7,452,190 B2 | 11/2008 | Bouton |
| 7,505,869 B2 | 3/2009 | Hartlaub |
| 7,621,878 B2 * | 11/2009 | Ericson et al. ............... 600/561 |
| 2001/0034502 A1 | 10/2001 | Moberg |
| 2002/0040208 A1 | 4/2002 | Flaherty |
| 2002/0072733 A1 | 6/2002 | Flaherty |
| 2002/0077581 A1 | 6/2002 | Davidner |
| 2002/0087115 A1 | 7/2002 | Hartlaub |
| 2002/0107477 A1 | 8/2002 | Kipfer |
| 2002/0120236 A1 | 8/2002 | Diaz |
| 2002/0173773 A1 | 11/2002 | Olsen |
| 2003/0073954 A1 | 4/2003 | Moberg |
| 2003/0078547 A1 | 4/2003 | Shekalim |
| 2003/0088238 A1 | 5/2003 | Poulsen |
| 2003/0125662 A1 | 7/2003 | Bui |
| 2003/0135154 A1 | 7/2003 | Heiniger |
| 2003/0236489 A1 | 12/2003 | Jacobson |
| 2004/0044305 A1 | 3/2004 | Hughett |
| 2004/0085215 A1 | 5/2004 | Moberg |
| 2004/0087894 A1 | 5/2004 | Flaherty |
| 2004/0127844 A1 | 7/2004 | Flaherty |
| 2004/0220548 A1 | 11/2004 | Heruth et al. |
| 2004/0260233 A1 | 12/2004 | Garibotto |
| 2004/0260234 A1 | 12/2004 | Srinivasan |
| 2005/0075624 A1 * | 4/2005 | Miesel ................. 604/505 |
| 2005/0090799 A1 | 4/2005 | Morris |
| 2005/0123420 A1 | 6/2005 | Richter et al. |
| 2005/0192529 A1 | 9/2005 | Butterfield |
| 2005/0209512 A1 | 9/2005 | Heruth et al. |
| 2005/0209513 A1 | 9/2005 | Heruth et al. |
| 2005/0222643 A1 * | 10/2005 | Heruth et al. ................. 607/48 |
| 2005/0234514 A1 | 10/2005 | Heruth et al. |
| 2005/0234518 A1 | 10/2005 | Heruth et al. |
| 2005/0241387 A1 * | 11/2005 | Miesel et al. .............. 73/204.21 |
| 2005/0245858 A1 | 11/2005 | Miesel |
| 2005/0267413 A1 | 12/2005 | Wang |
| 2006/0161376 A1 | 7/2006 | Hartlaub |
| 2006/0271029 A1 | 11/2006 | Abboud |
| 2007/0060871 A1 | 3/2007 | Istoc |
| 2007/0078381 A1 | 4/2007 | Yap |
| 2007/0149926 A1 | 6/2007 | Moberg |
| 2007/0191770 A1 | 8/2007 | Moberg |
| 2007/0270782 A1 | 11/2007 | Miesel |
| 2007/0274843 A1 | 11/2007 | Vanderveen |
| 2008/0009837 A1 * | 1/2008 | Miesel ................. 604/891.1 |
| 2008/0097287 A1 | 4/2008 | Nelson |
| 2008/0139996 A1 | 6/2008 | Bowman |
| 2008/0167641 A1 | 7/2008 | Hansen |
| 2009/0082757 A1 | 3/2009 | Rogers |

FOREIGN PATENT DOCUMENTS

| | | |
|---|---|---|
| EP | 0 248 633 A2 | 12/1987 |
| EP | 0 248 633 A3 | 2/1989 |
| EP | 0 248 632 A3 | 3/1989 |
| EP | 0 328 162 A2 | 8/1989 |
| EP | 0 328 162 A3 | 10/1989 |
| EP | 0 328 162 B1 | 2/1993 |
| EP | 0 248 633 B1 | 8/1994 |
| EP | 0 522 527 | 12/1994 |
| EP | 0 856 326 A1 | 8/1998 |
| EP | 0 621 791 | 8/2000 |
| EP | 1 342 481 | 9/2003 |
| EP | 1 535 637 | 6/2005 |
| EP | 0 993 268 | 11/2005 |
| EP | 1 839 695 | 10/2007 |
| EP | 1 592 468 | 9/2008 |
| WO | WO 95/32013 | 11/1995 |
| WO | WO 99/55225 | 11/1999 |
| WO | WO 00/44420 | 8/2000 |
| WO | WO 02/064040 A2 | 8/2002 |
| WO | WO 02/070047 | 9/2002 |
| WO | WO 02/064040 A2 | 11/2002 |
| WO | WO 02/064040 A3 | 5/2003 |
| WO | WO 2005/072792 | 8/2005 |
| WO | WO 2005/089860 A1 | 9/2005 |
| WO | WO 2005/119181 | 12/2005 |
| WO | WO 2006/067217 | 6/2006 |
| WO | WO 2006/108775 | 10/2006 |
| WO | WO 2007/020029 A1 | 2/2007 |

OTHER PUBLICATIONS

U.S. Appl. No. 11/731,355, filed Mar. 30, 2007, Miesel et al.
International Preliminary Report and Written Opinion on Patentability for PCT/US2008/057792; 8 pgs.
International Search Report for PCT/US2008/057792; 4 pgs.
U.S. Appl. No. 12/623,484, filed Nov. 23, 2009.
U.S. Appl. No. 11/731,355, filed Mar. 30, 2007.
U.S. Appl. No. 11/778,400, filed Jul. 16, 2007.

* cited by examiner

CATHETER MALFUNCTION DETERMINATIONS USING PHYSIOLOGIC PRESSURE

TECHNICAL FIELD

The present invention relates generally to systems and methods for identifying malfunctions in the implanted catheter of an infusion system by sensing fluid pressure within the catheter.

BACKGROUND

Infusion systems may be used, for example, when administration of a therapeutic substance (e.g., a pharmaceutically active agent) to an internal delivery site within a patient is desired. The internal delivery sites may include, e.g., vascular delivery (arterial, venous, etc.), intraparenchymal solid organ sites (e.g., Ipa brain, liver, etc.), intrathecal locations (containing the cerebrospinal fluid (CSF) of a patient), etc. An implantable infusion system including a catheter may be preferred when it is important to deliver the therapeutic substance to the internal delivery site in controlled, often minute, dosages.

Typically, an infusion system includes a reservoir containing a supply of therapeutic substance awaiting delivery to a the patient. A pump may be fluidly coupled to the reservoir for creating fluidic pressure to facilitate delivery of the therapeutic substance to the patient. A catheter provides a pathway for delivering the therapeutic substance to the internal delivery site of the patient. All parts of the infusion system need to operate adequately to ensure proper delivery of therapeutic substances using the system.

While perhaps the least complex component of an infusion system, catheters can have and/or can develop operational problems. For example, catheters may be placed in the wrong location when originally deployed or the catheters may move (migrate) over time such that fluids (e.g., therapeutic substances) delivered through the catheters are not delivered to the selected internal delivery site.

Catheters can also become obstructed or clogged during use. A partial or complete blockage could prevent the therapeutic substance from reaching the selected delivery site of the patient or, in the case of a partial obstruction, could prevent an adequate supply of the therapeutic substance from reaching the internal delivery site of the patient.

Catheters can also leak due to cuts, tears, etc. A leak, small or large, can also prevent the therapeutic substance from reaching the selected internal delivery site of the patient. In addition to the lack of therapeutic substance supplied to the selected internal delivery site of the patient, the therapeutic substance could be dispersed outside of the selected internal delivery site which may create further issues.

SUMMARY OF THE INVENTION

The present invention provides a variety of methods of determining whether an implanted catheter used to deliver fluids to the selected internal delivery site of a patient is not properly located or has migrated away from the selected internal delivery site, is leaking, is blocked, etc. The determination is made by analyzing the pressure modulation of fluid within the catheter and determining whether the pressure of the fluid in the catheter is modulated by physiologic pressure changes present at the selected internal delivery site.

The selected internal delivery site may include, e.g., any fluid-filled internal space in the body, including, but not limited to the intrathecal space (where the intrathecal space contains the CSF of the patient, blood vessels, etc.). Other potential internal delivery sites may include, e.g., solid (parenchymal) organs, hollow (luminal) organs, etc. The physiologic pressure changes at the selected internal delivery site may be caused by, e.g., cardiac activity, respiration, changes in patient posture, etc.

When a catheter is properly located with an infusion section positioned at the selected internal delivery site, pressure modulations at the selected internal delivery site are preferably transmitted to the fluid in the catheter. When pressure measurements of the fluid in the catheter exhibit pressure modulations similar to the expected physiologic pressure modulations, it may be possible to determine that a catheter malfunction does not exist, i.e., that the infusion section of the catheter is located at the selected internal delivery site and that the catheter itself is not leaking or blocked. Conversely, the absence of expected physiological pressure modulations in the fluid within the catheter (as caused by, e.g., cardiac activity, respiration, changes in patient posture, etc.), may serve as the basis for a determination that the catheter has malfunctioned, e.g., that the infusion section of the catheter is not located at the selected internal delivery site (e.g., within the CSF, etc.), is leaking, is blocked, etc.

The pressure modulation profiles developed based on the fluid pressure measured within the catheter may be analyzed using a variety of techniques. For example, the pressure modulation profile may be compared to a selected pressure profile to determine whether the pressure modulation profile includes physiological pressure modulation as a component. In another example, the pressure modulation profile may be analyzed to determine if the pressure modulation profile includes physiological pressure modulation caused by patient cardiac activity. In another alternative, the pressure modulation profile may be analyzed to determine if the pressure modulation profile includes physiological pressure modulation caused by patient respiration. In still another example, the pressure modulation profile may be analyzed to determine if the pressure modulation profile includes physiological pressure modulation caused by patient activity (e.g., movements from the supine to upright postures, etc.).

Although the methods of the present invention could potentially be performed continuously, it may be advantageous (from, e.g., a power conservation standpoint) if the pressure modulation measurement, data collection, and/or analyses were performed at selected times. The selected times may include, e.g., at a predetermined time (on, e.g., a daily/weekly/monthly basis), at the request or direction of an individual (the patient, a caregiver, physician, health care monitoring service, etc.), or on any other suitable basis. If the measurement and/or analyses are to be performed at the request or direction of an individual, the commands required to initiate the process may be delivered using, e.g., remote administration systems such as telemetry, wireless networks, etc.

As discussed herein, the pressure modulation profiles are based on the measured pressure of fluids within the catheters. Although the fluids may preferably contain one or more therapeutic substances that are to be delivered to the patient through the catheter, the fluids are not required to contain any therapeutic substances. For example, the fluids may be supplied only to confirm proper catheter placement and/or operation without supplying any specific therapeutic effect.

It may be preferred that the pressure modulation profiles used in connection with the present invention are based on measurements of the fluid in the catheter that are taken when the fluid is stationary within the lumen of the catheter. Pressure modulation profiles obtained when the fluid is stationary may be preferred to limit pressure modulation caused by, e.g., movement of the fluid as it passes through the catheter (as driven by a pump or other fluid delivery mechanism). Such unwanted pressure modulation may potentially interfere with accurate assessment of the presence of catheter malfunctions based on measured fluid pressure.

When it is determined that a catheter malfunction exists, a variety of actions may be taken. In some instances, an alert may be provided to the patient and/or a third party after determining the existence of the catheter malfunction. The alert may take any suitable form, e.g., audible, visual, tactile (e.g., vibrations, etc.). Another action that may be taken in response to a catheter malfunction is that the delivery of fluid (including, e.g., a therapeutic substance) to the lumen of the catheter may be terminated after determining the existence of a catheter malfunction.

The pressure modulation profiles used in connection with the present invention may be developed based on pressure measurements obtained over only selected time intervals. The intervals may have a duration of, e.g., 5 minutes or less, 1 minute or less, etc. over which the pressure is monitored. Although the pressure measurements may be taken continuously, it may be preferred to use only the pressure data generated during the selected time interval(s) to develop the pressure modulation profiles used in connection with the invention. The selected time intervals may be chosen based at least in part on the patient's circadian rhythm (e.g., when a patient is sleeping, etc.). In another alternative, the selected time intervals may be selected based on manual or other input during a troubleshooting procedure, routine checkup session, etc.

The methods of the present invention may also involve the storage of data representative of the pressure modulation profile in a data storage device before comparing the pressure modulation profile to a selected pressure profile or performing any other analyses on the pressure modulation profile to determine the patency of the catheter. In those embodiments in which the data is stored, any such analyses may be performed within the system itself (using, e.g., a self-contained controller) or the analyses may be performed external to the system by, e.g., transmitting the data to an external device (using, e.g., telemetry, etc.).

As discussed herein, the methods may be performed in real-time or the pressure data may be stored to allow for analysis at a later time. If performed in real-time, the infusion system may preferably include hardware and/or software to allow for the required functions.

In one aspect, the present invention provides a method of identifying the presence of a catheter malfunction in an implanted catheter by measuring pressure of a fluid located within a lumen in a catheter implanted in a patient, wherein the lumen extends to an infusion section that is located at a selected internal delivery site in the patient; developing a pressure modulation profile based on the measured pressure of the fluid in the lumen; and comparing the pressure modulation profile to a selected pressure profile.

In another aspect, the present invention provides a method of identifying the presence of a catheter malfunction in an implanted catheter by measuring fluid pressure of a fluid located within a lumen in a catheter implanted in a patient, wherein the lumen extends to an infusion section that is located at a selected internal delivery site in the patient; developing a pressure modulation profile based on the measured fluid pressure of the fluid in the lumen; and determining if the pressure modulation profile includes pressure modulation caused by patient cardiac activity.

In another aspect, the present invention provides a method of identifying the presence of a catheter malfunction in an implanted catheter by measuring fluid pressure of a fluid located within a lumen in a catheter implanted in a patient, wherein the lumen extends to an infusion section that is located at a selected internal delivery site in the patient; developing a pressure modulation profile based on the measured fluid pressure of the fluid in the lumen; and determining if the pressure modulation profile includes pressure modulation caused by patient respiration.

In another aspect, the present invention provides an implantable infusion system that includes a pump mechanism fluidly coupled to a reservoir to receive fluid contained within the reservoir; a catheter having a delivery lumen fluidly coupled to the pump mechanism, wherein the delivery lumen extends to an implantable infusion section in the catheter; a pressure sensor positioned to monitor fluid pressure within the delivery lumen of the catheter and provide a pressure signal representative of the fluid pressure; and control electronics connected to receive the pressure signal from the pressure sensor, wherein the control electronics develops a pressure modulation profile based on the fluid pressure measured in the delivery lumen and compares the pressure modulation profile to a selected pressure profile.

In another aspect, the present invention provides an implantable infusion system that includes a pump mechanism fluidly coupled to a reservoir to receive fluid contained within the reservoir; a catheter comprising a delivery lumen fluidly coupled to the pump mechanism, wherein the delivery lumen extends to an implantable infusion section in the catheter; a pressure sensor positioned to monitor fluid pressure within the delivery lumen of the catheter and provide a pressure signal representative of the fluid pressure; and control electronics connected to receive the pressure signal from the pressure sensor, wherein the control electronics develops a pressure modulation profile based on the fluid pressure measured in the delivery lumen and determines if the pressure modulation profile includes pressure modulation caused by patient cardiac activity.

In another aspect, the present invention provides an implantable infusion system that includes a pump mechanism fluidly coupled to a reservoir to receive fluid contained within the reservoir; a catheter comprising a delivery lumen fluidly coupled to the pump mechanism, wherein the delivery lumen extends to an implantable infusion section in the catheter; a pressure sensor positioned to monitor fluid pressure within the delivery lumen of the catheter and provide a pressure signal representative of the fluid pressure; and control electronics connected to receive the pressure signal from the pressure sensor, wherein the control electronics develops a pressure modulation profile based on the fluid pressure measured in the delivery lumen and determines if the pressure modulation profile includes pressure modulation caused by patient respiration.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

It is noted that the terms "comprises" and variations thereof do not have a limiting meaning where these terms appear in the accompanying description and claims. Moreover, "a," "an," "the," "at least one," and "one or more" are used interchangeably herein.

As discussed herein, the methods and systems of the present invention involve monitoring fluid pressure within the fluid-filled lumen of a catheter where the fluid in the lumen is in fluid communication with the physiological pressure at a selected internal delivery site. The infusion section of the catheter is preferably located at the selected internal delivery site such that pressure modulations experienced at the selected internal delivery site can be transmitted to the fluid in the catheter lumen. A pressure sensor operably connected to the catheter to measure fluid pressure within the catheter lumen will, therefore, preferably be capable of measuring the pressure modulations transmitted into the fluid in the lumen at the selected internal delivery site.

Although the following description of illustrative embodiments focuses on an internal delivery site that is located within the intrathecal space of the patient (where the intrathecal space is the space that contains the CSF of the patient), it should be understood that the methods and systems of the present invention may be used in connection with a catheter having an infusion section located at any selected internal delivery site at which physiological pressure modulations may be used to determine the existence of catheter malfunctions as discussed herein. Examples of some alternative internal delivery sites may include, e.g., any fluid-filled internal space in the body, including, but not limited to the blood vessels, etc. Other potential internal delivery sites may include, e.g., solid (parenchymal) organs, hollow (luminal) organs, etc.

Figure 1:
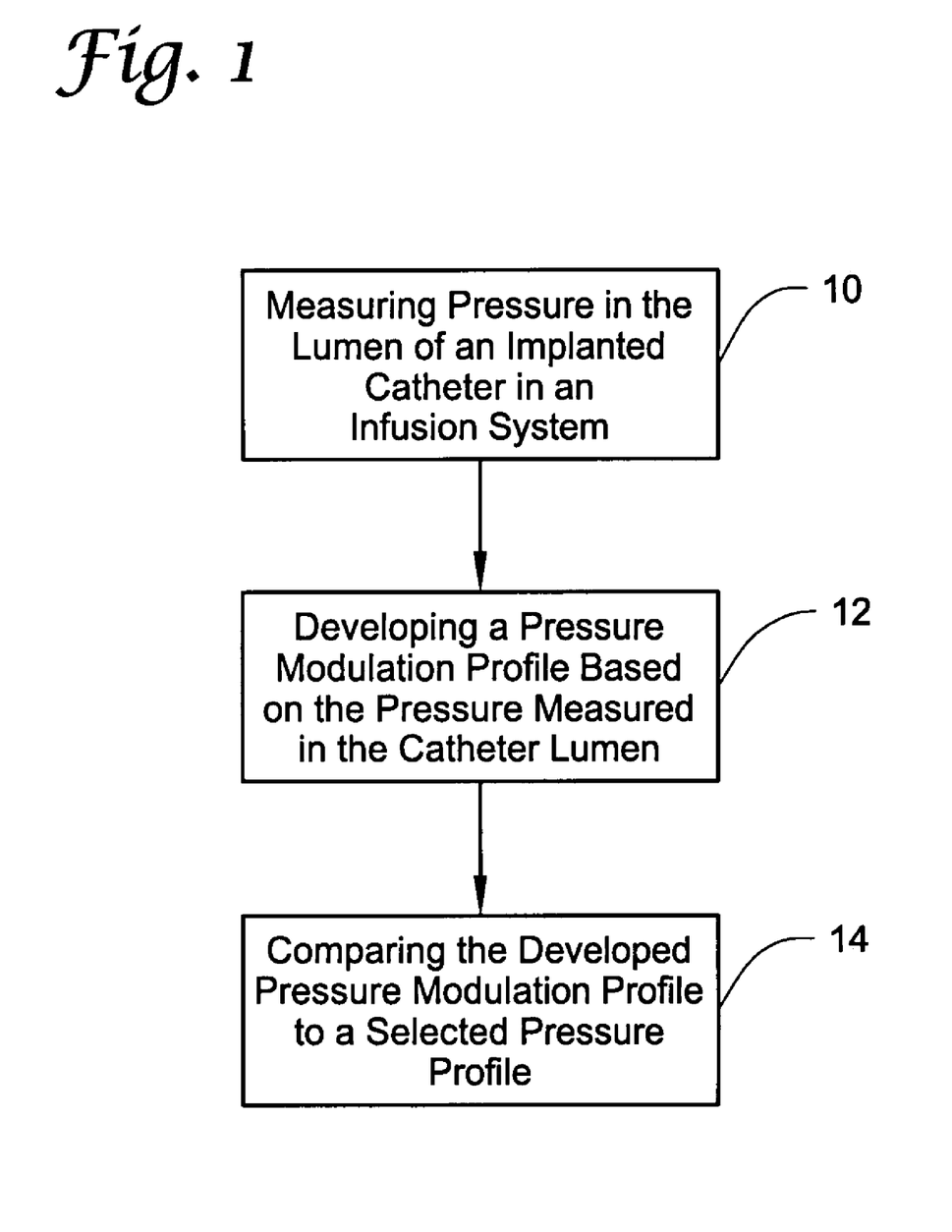
FIG. 1 is a flow diagram of one exemplary method according to the present invention.

FIG. 1 is a flowchart of one exemplary method according to the present invention. The method involves measuring pressure of a fluid within the catheter lumen of an infusion system that includes a catheter having an infusion section implanted within a patient (box 10 in FIG. 1). The method also includes developing a pressure modulation profile based on the measured fluid pressure (box 12 in FIG. 1). The pressure modulation profile is then compared to a selected pressure profile (box 14 in FIG. 1). Based on the comparison, a determination can be made whether or not a catheter malfunction has occurred where the developed pressure modulation profile differs from the selected pressure profile. The differences between the developed pressure modulation profile may preferably include the presence or absence of physiological pressure modulations in the developed pressure modulation profile.

Figure 2:
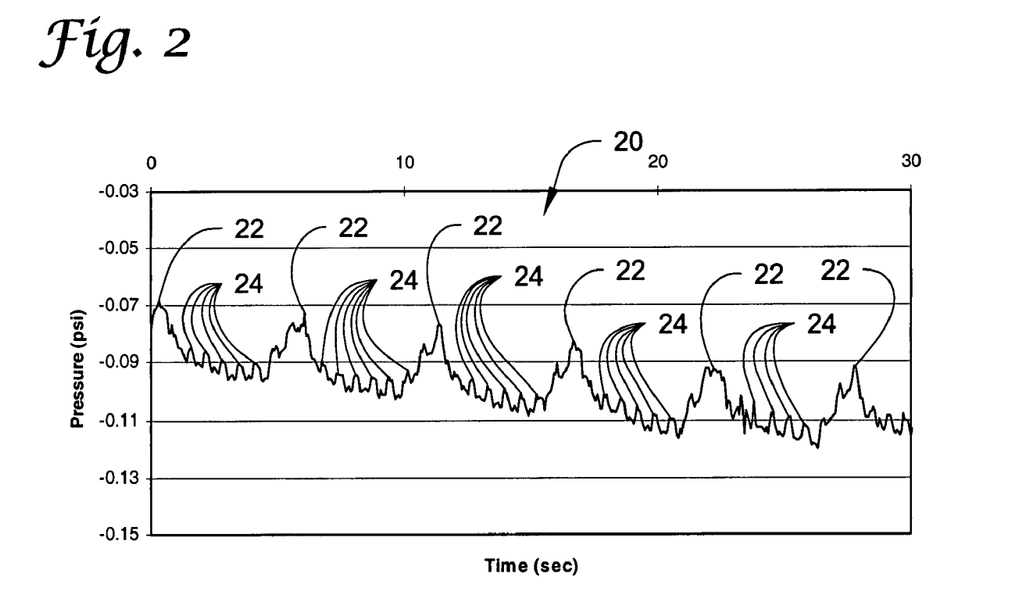
FIG. 2 is a graph of fluid pressure (y-axis) versus time (x-axis) in a catheter having an infusion section located within the CSF in the intrathecal space of a subject.
Figure 3:
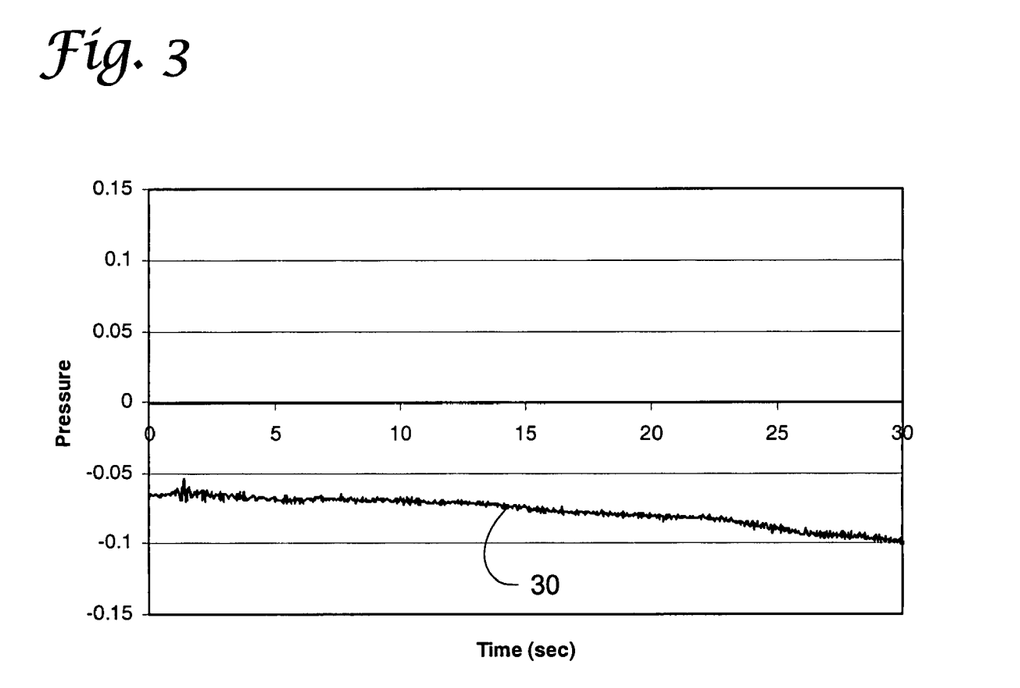
FIG. 3 is a graph of fluid pressure (y-axis) versus time (x-axis) in a catheter having an infusion section located outside of the intrathecal space of a subject.

FIGS. 2 & 3 depict various pressure modulation profiles to illustrate the principles upon which the methods and systems of the present invention are based. The pressure within the CSF located in the intrathecal space (which is one example of a potentially suitable selected internal delivery site) varies with physiological activity of a patient. The data plotted in FIG. 1 demonstrates those variations, where the plot 20 represents pressure of fluid within a lumen located in fluid communication with the CSF and includes major peaks 22 representative of patient respiration activity and minor peaks 24 representative of cardiac activity (i.e., heartbeats). The major peaks 22 and minor peaks 24 are transmitted into the fluid in the lumen from the CSF (into which the lumen opens).

In contrast, the data plotted in FIG. 3 demonstrates the pressure recorded within the fluid of the lumen when the opening (e.g., infusion section) of the lumen is located outside of the intrathecal space. As seen in plot 30 of FIG. 3, the pressure profile of the fluid located within the lumen when the opening is located outside of the intrathecal space is not noticeably modulated by physiological activity (such as, e.g., respiration or cardiac activity). It is theorized that the interstitial fluid pressure, i.e., the fluid pressure within the body but outside of any enclosed system (e.g. fluid-filled space (such as a blood vessel, intrathecal space, etc.), in an organ, etc.) is relatively constant throughout the body. When a catheter lumen opens within this interstitial space, significant pressure modulations are not typically observed in the lumen—with the resulting pressure modulation profile appearing similar to that depicted in FIG. 3. Pressure modulation profiles for catheters that are blocked or are leaking within the interstitial space will also not typically include modulations indicative of physiological pressure modulations.

FIGS. 2 & 3 depict pressure measurements as a function of time to illustrate the principles of the present invention. It should be understood that these pressure curves are exemplary in nature only. Although scales may be included, the systems and methods of the present invention are not limited to catheters in which these same pressures are developed. Rather, the profiles or shapes of the pressure curves may be used to identify catheter malfunctions in connection with the present invention.

Although physiological pressure modulations may be caused by respiration and/or cardiac activity at the selected internal delivery site, other physiological pressure modulations may be caused by, e.g., changes in posture. For example, as a patient moves from a horizontal (e.g., supine, prone, etc.) position to an upright position, the spinal column of a human moves from a generally horizontal orientation to a generally vertical orientation. In response to such posture changes, the fluid head of the CSF within the intrathecal space will change. Fluid-head pressure modulations caused by posture changes will typically be greater towards the lower end of the spinal column due to the larger volume of CSF located above the lower end of the spinal column when the spinal column is generally vertical. Such physiological pressure modulations may be controlled by directing a patient to change posture and measuring/detecting the resulting pressure modulations.

One or more of these physiological pressure modulations may be used to determine if the infusion section of the catheter is located at the selected internal delivery site (e.g., within the intrathecal space). If the infusion section is located at the selected internal delivery site, then the fluid pressure of fluid within the catheter lumen will be modulated by the physiological pressure modulations present at the selected internal delivery site. Conversely, if the infusion section of the catheter is not located at the selected internal delivery site (due to misplacement, migration after placement, etc.), then the pressure of the fluid within the catheter lumen will not exhibit modulations caused by the physiological pressure modulations that are present at the selected internal delivery site.

In some embodiments, it may be desirable to halt any flow of fluid (e.g., therapeutic substance) into the catheter when measuring the pressure of the fluid within the lumen to reduce the influence of pump pressure modulations on the pressure of the fluid within the lumen. This may be particularly true if the fluid is delivered using pulsed delivery methods, peristaltic pumps, etc. that could, themselves, cause pressure modulations.

The pressure measurements used to develop pressure modulation profiles may be taken over selected time intervals where the selected intervals may coincide with a variety of activities. For example, the selected intervals may occur when no fluid is being delivered through the catheter such that the fluid within the catheter is stationary. The selected intervals may also be chosen based at least in part on the patient's circadian rhythm (e.g., when a patient is sleeping, etc.). Determination as to whether a patient is sleeping (or resting in, e.g., the supine, prone or another generally horizontal position) may be made based on external input (e.g., a clock, an indicator activated by the patient or a third party, etc.). Alternatively, the system and method may be adaptive. In an adaptive system/method, fluid head pressure changes that occur as a result of movements between the upright and horizontal postures may be used to determine whether the patient is sleeping (or otherwise resting). Other methods and/or systems for determining when a patient is sleeping or resting may be described in, e.g., U.S. Patent Application Publication No. US 2005/0209512 (DETECTING SLEEP); U.S. Patent Application Publication No. US 2005/0209513 (COLLECTING SLEEP QUALITY INFORMATION VIA A MEDICAL DEVICE); U.S. Patent Application Publication No. US 2005/0234514 (COLLECTING POSTURE INFORMATION TO EVALUATE THERAPY); and U.S. Patent Application Publication No. US 2005/0234518 (COLLECTING ACTIVITY AND SLEEP INFORMATION VIA A MEDICAL DEVICE).

Because the methods and systems that are developed to identify a catheter malfunction are based on determining whether or not the pressure of fluid delivered through the catheter is modulated by physiological pressure modulations at the selected internal delivery site, the methods may involve a variety of different analyses. Those analyses may include, e.g., comparing the pressure modulation profile to a selected pressure profile where the selected pressure profile includes physiological pressure modulations. Potential analytical methods may include, e.g., direct observation of the pressure modulation profile (e.g., on a display), comparison of the pressure modulation profile to a selected pressure profile (using, e.g., a look-up table, etc.), etc. In some methods, the physiological events that impact the pressure modulation profile may be tracked and correlated to changes in the pressure modulation profile (e.g., heart rate may be monitored, respiration may be monitored (using, e.g., thoracic impedance, etc.).

The selected pressure profile used in connection with some embodiments of the invention may, for example, include physiological modulations based on patient respiration and/or cardiac activity. In other embodiments, the selected pressure profile may include physiological pressure modulations based on changes in posture (e.g., movement from an upright posture where the patient is sitting/standing to a horizontal posture where the patient is, e.g., lying down on a horizontal surface—or vice versa). The absence of the selected physiological pressure modulations in the developed pressure modulation profile could be one indicator that a catheter malfunction has occurred.

In some embodiments the selected pressure profile may not include physiological pressure modulations. If the selected pressure profile does not include physiological pressure modulations, then the comparison may be made to determine if the developed pressure modulation profile contains physiological pressure modulations that are not present in the selected pressure profile. If it does, then a determination can be made that the infusion section of the catheter is located at the selected internal delivery site (e.g., in the CSF). In other words, the systems/methods can be compared to selected pressure profiles that do or do not include physiological pressure modulations to assist in determining the existence or absence of a catheter malfunction.

Among the catheter malfunctions that may result in an absence of expected physiological pressure modulations in the developed pressure modulation profile is that the infusion section of the catheter is not located at the selected internal delivery site (e.g., in the CSF). Such a condition may occur when, for example, the infusion section is placed outside of the selected internal delivery site (e.g., the intrathecal space) when originally implanted. Alternatively, the infusion section may be properly located at the selected internal delivery site (e.g., within the intrathecal space) as originally deployed, but may have migrated away from the selected internal delivery site (e.g., outside of the intrathecal space) such that the expected physiological pressure modulations are not detected after the initial deployment.

Another catheter malfunction that may cause an absence of physiological pressure modulations in the developed pressure modulation profile is that the catheter lumen may become blocked downstream from the location at which pressure is measured such that physiological pressure modulations at the selected internal delivery site (e.g., from the CSF) cannot be transmitted to the pressure sensor. Such a blockage would also typically be expected to prevent or significantly limit the delivery of any fluids through the catheter.

Still another malfunction that may cause an absence of physiological pressure modulations in the developed pressure modulation profile is a leak in the catheter lumen. To limit the presence of physiological pressure modulation in the catheter, the leak may typically be located outside of the selected internal delivery site (e.g., outside of the intrathecal space, blood vessels, selected organ, etc.) because a leak within the same general region of the selected internal delivery site (e.g., within the intrathecal space, blood vessels, selected organ, etc.) could still result in the transmission of expected physiological pressure modulations to the pressure sensor. Also, it should be noted that smaller leaks may not be detectable using the methods and systems of the present invention. A leak occurring outside of the selected internal delivery site would also typically be expected to prevent or significantly limit the delivery of any fluids to the selected internal delivery site.

If it is determined that a catheter malfunction exists, a variety of actions may be taken. For example, the delivery of fluid through the catheter may be terminated, the rate of delivery of the fluid may be changed, etc. In addition to, or in place of, terminating or changing the fluid delivery rate, other actions may be taken. For example, an alert may be provided to the patient and/or a third party (caregiver, medical personnel, etc.). The alert may be provided locally in the form of an audible signal (e.g., a buzzer), visual signal (e.g., a light), tactile signal (e.g., vibrations), etc. The alert may, in some embodiments be transmitted from the infusion system to another device, e.g., personal computer, wireless computer/telephone network, modem, etc.

Figure 4:
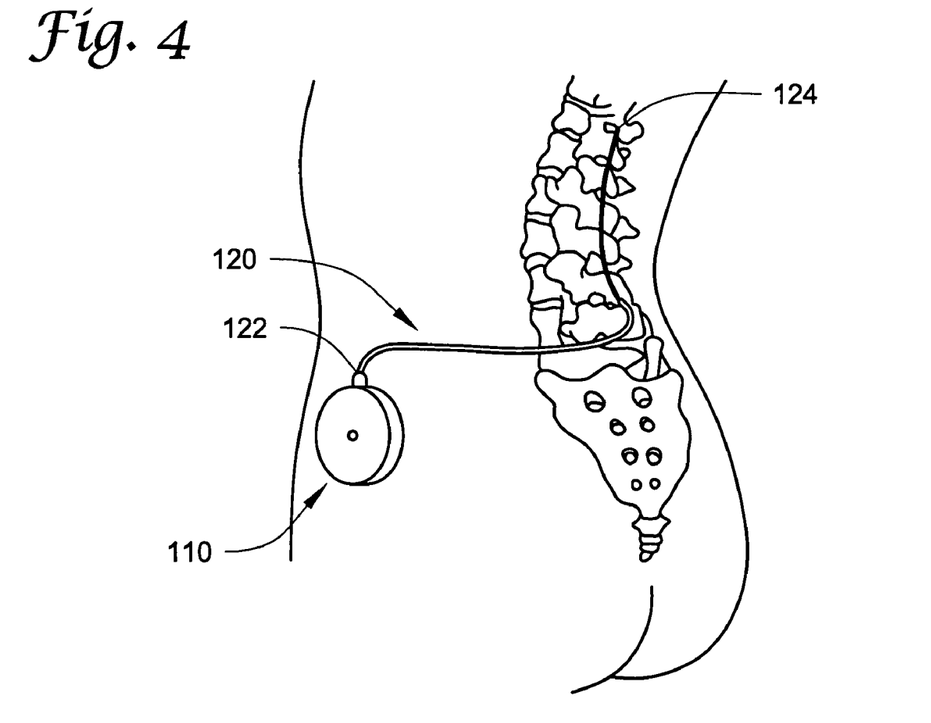
FIG. 4 depicts one exemplary implanted infusion system according to the present invention.

Although many different infusion systems could be used to practice the methods of the present invention, some exemplary infusion systems will be described herein. FIG. 4 illustrates one exemplary embodiment of an implantable infusion system that may be used in connection with the present invention. The depicted infusion system is implanted within a patient's body. Infusion systems may be used for a wide variety of therapies including treatment of pain, spasticity, and other medical conditions. Although exemplary infusion systems that may be used in connection with the present invention are described herein, reference may also be had to U.S. Patent Application Publication No. US 2005/0075624 A1, titled PRESSURE SENSING IN IMPLANTABLE MEDICAL DEVICES (Miesel).

The infusion systems and methods of the invention are preferably capable of infusing a fluid from a reservoir to the selected internal delivery site (e.g., the CSF, etc.) through a catheter having an infusion section positioned at the selected internal delivery site (e.g., within the intrathecal space containing the CSF). Although the fluid may preferably contain one or more therapeutic substances that are to be delivered to a patient through the catheter, the fluids are not required to contain any therapeutic substances. For example, the fluids may be used within the methods and systems to confirm proper catheter functioning without supplying any specific therapeutic effect.

As used herein, the term "therapeutic substance" means a substance intended to have a therapeutic effect on the patient, e.g., pharmaceutical compositions, genetic materials, biologics, and other substances. "Pharmaceutical compositions," as used herein, may include chemical formulations intended to have a therapeutic effect such as antispasmodics, pain medications, chemotherapeutic agents, and the like. Pharmaceutical compositions are often configured to function effectively in an implanted environment by possessing various characteristics including: stability at body temperature to retain therapeutic qualities; concentration to reduce the frequency of replenishment; and the like. "Genetic materials," as used herein, may include substances intended to have a direct or indirect genetic therapeutic effect such as genetic vectors, genetic regulator elements, genetic structural elements, DNA, and the like. "Biologics," as used herein, may include substances that are living matter, or derived from living matter, and offer a therapeutic effect to the patient such as stem cells, platelets, hormones, biologically produced chemicals, and the like. "Other substances" may include most any other substance that is intended to have a therapeutic effect, yet does not clearly fit within one of the categories identified above. Examples of other substances may include saline solutions, fluoroscopy agents, and the like.

The exemplary infusion system depicted in FIG. 4 includes an infusion pump assembly 110 and catheter 120 having a proximal end 122 attached to the pump assembly 110. The pump assembly 110 may preferably be surgically implanted subcutaneously in the pectoral, abdominal or other region of the subject's body. The distal end 124 of the catheter 120 is preferably implanted in a patient such that the distal end 124 is located at the selected internal delivery site in the patient (in the intrathecal space of the patient as depicted in FIG. 4). The pump assembly 110 also preferably includes a reservoir that contains a fluid (e.g., a therapeutic substance) to be infused using the system. The fluid contained within the reservoir may preferably be replenished periodically using known techniques and structures.

Although the present invention also includes embodiments in which the catheter 120 is implanted with a proximal end outside the body of the patient so that it may attach to an external pump assembly, the remainder of this description is, for the sake of brevity, directed to implantable infusion systems that are entirely implanted in the body of the patient. As used herein, the term "implantable" means that at least a portion of the system, apparatus or device is adapted for implantation in the body of subject where it is located at least subcutaneously.

Although the infusion system of FIG. 4 is depicted as infusing a fluid into only one location in the intrathecal space, it should be understood that a single system could infuse one or more fluids to one or more selected internal delivery sites. Also, although depicted in connection with a human body, it should be understood that the infusion systems of the present invention could also be used on non-human animals.

The pump assemblies used in connection with the invention may include any suitable mechanism or structure capable of delivering one or more fluids to a patient. The structures used to drive fluids in the pump assemblies may be powered (e.g., piston pumps, diaphragm pumps, peristaltic pumps, etc.) or they may be activated based on pressure to drive fluid out of a reservoir (e.g., using collapsing diaphragms, expanding bladders, etc.). Examples of some potentially suitable pump assemblies may include, e.g., commercially available implantable infusion pumps such as, for example, the SYNCHROMED EL pumps, Models 8626 and 8627, manufactured by Medtronic, Inc., Minneapolis, Minn.

Figure 5:
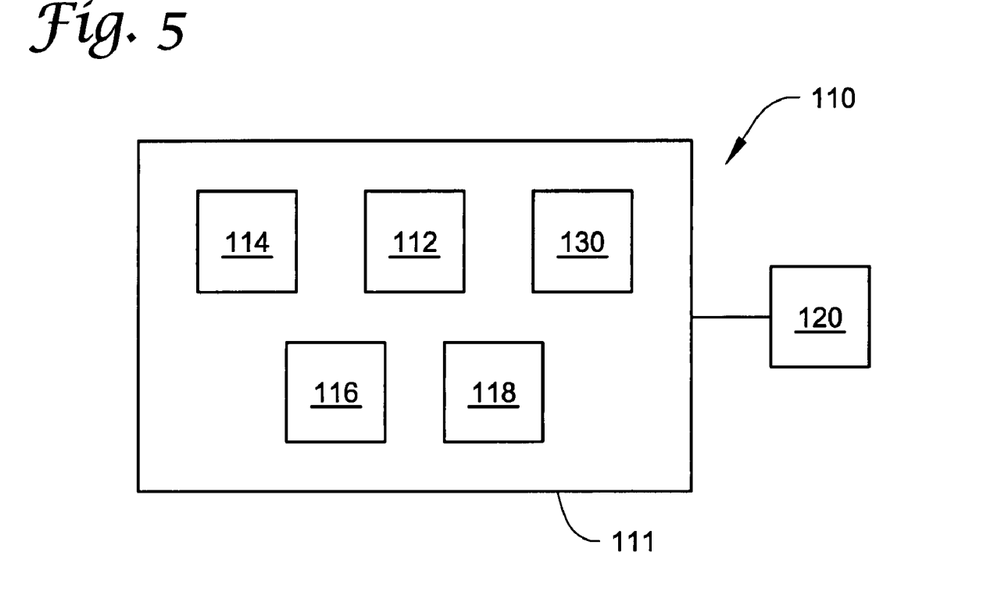
FIG. 5 is block diagram of the components in one exemplary infusion system according to the present invention.

The components of one exemplary pump assembly 110 are depicted in FIG. 5. The depicted pump assembly 110 may preferably include a pump mechanism 112 coupled to the catheter 120 such that fluid within the reservoir 114 can be delivered to the catheter 120 through the pump mechanism 112. The pump assembly 110 may also preferably include a power supply 116 and control electronics 118 connected to the power supply 116 and the pump mechanism 112 such that the infusion of fluids using the system can be controlled. Although not specifically depicted, the pump assembly 110 may also include other components such as, e.g., communication devices (e.g., telemetry modules, etc.) to provide for control and/or communication between the infusion system and external devices.

Another component depicted in FIG. 5 is a pressure sensor 130 that, in the depicted embodiment, is connected to the control electronics 118. The pressure sensor 130 is preferably connected to the catheter 120 in a manner that allows the pressure sensor 130 to measure the fluid pressure of fluid located within the catheter 120 and to provide a pressure signal (to, e.g., the control electronics 118) that is representative of the fluid pressure of the fluid in the catheter 120. Examples of some potentially suitable pressure sensors and their interconnection with control electronics 118 may be described in, e.g., U.S. Patent Application Publication No. US 2005/0075624 (Miesel) titled PRESSURE SENSING IN IMPLANTABLE MEDICAL DEVICES.

Figure 6:
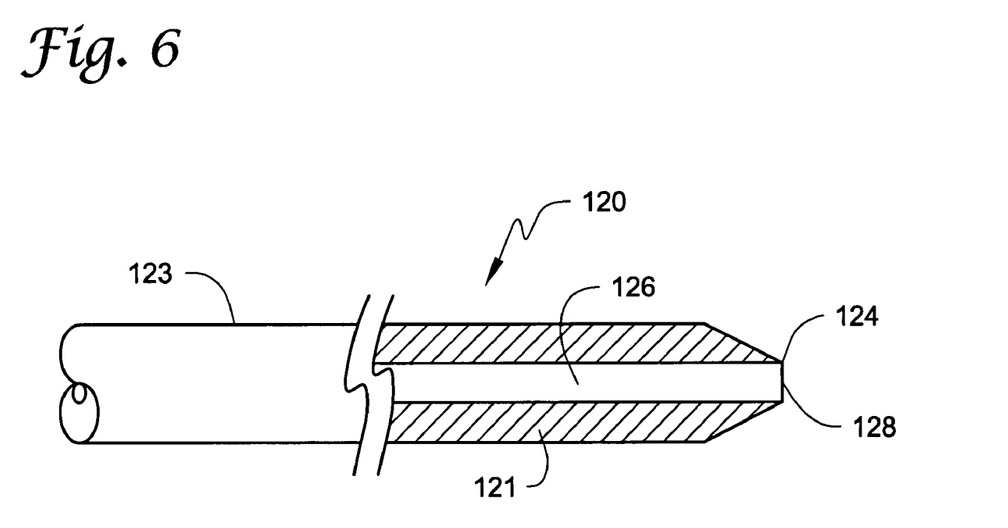
FIG. 6 is an enlarged partial cross-sectional view of a catheter that may be used in connection with the methods and infusion systems of the present invention.

FIG. 6 depicts a portion of the catheter 120 in an enlarged cross-sectional view. The catheter 120 includes an elongated tubular portion 123 that preferably extends from the proximal end (not shown) to the distal end 124. The catheter 120 depicted in FIG. 6 includes a lumen 126 that terminates at opening 128 at the distal end 124. Therapeutic substances (or other fluids) delivered from the pump assembly 110 to the catheter 120 pass through lumen 126 and preferably exit the catheter 120 through opening 128.

The body of catheter 120 may preferably be constructed of any suitable material, e.g., an elastomeric tube. Examples of some suitable materials include, but are not limited to, silicone rubber (e.g., polydimethyl siloxane) or polyurethane, both of which can provide good mechanical properties and are very flexible. Suitable materials for the catheter 120 are also preferably chemically inert such that they will not interact with therapeutic substances, body tissues, or body fluids while implanted in the patient.

Where the catheter is to be used for intrathecal fluid delivery, it may be preferred that at least a portion of the catheter 120 be sized to fit in the gap between the spinal cord and the dura within the intrathecal space. Catheters intended for delivering fluids to other internal delivery sites will be sized appropriately for those locations. As another consideration in sizing the catheter, the diameter of the lumen 126 is preferably large enough to accommodate expected infusion rates with acceptable flow resistance. The wall 121 of the catheter 120 is preferably thick enough to withstand normal handling during the implant procedure and forces from body tissues during normal motion. As an example, a catheter intended for use in intrathecal fluid delivery may have an outside diameter of 1.25 millimeters (mm), an inside diameter of 0.5 mm, and a wall thickness of 0.375 mm. Such a catheter may have a length of, e.g., 50 centimeters (cm) long to reach from, e.g., a drug infusion pump implanted in the patient's abdomen to the spine.

Although the opening 128 through which the fluid exits the catheter 120 is depicted as a simple opening in the distal end 124 of catheter 120, the opening 128 is only one embodiment of an infusion section that may be provided in catheters used in connection with the present invention. Other embodiments of infusion sections may be may include, e.g., multiple openings, permeable membranes, etc. Although the infusion section (opening 128) of the depicted catheter 120 is located at the distal end 124 of the catheter 120, the infusion section(s) may be positioned at any location along the length of the catheter 120 that can be used to deliver the fluid to the selected internal delivery site. Examples of some potentially suitable catheters with a variety of infusion sections may be described in, e.g., U.S. Patent Application Publication No. US 2004/0220548, titled PERMEABLE MEMBRANE CATHETERS, SYSTEMS AND METHODS.

Because physiological pressure modulations at the selected internal delivery site are preferably transmitted into the fluid located within the lumens of catheters used in connection with the invention, the construction of the infusion sections is preferably selected to provide for that pressure transmission. In other words, the infusion sections used in connection with the present invention are preferably capable of transmitting physiological pressure modulations (e.g., from the CSF where the infusion sections may be located) into the fluid located within the catheter lumen.

The components of the pump assembly 110 to which the catheter 120 is connected may be contained within a single housing 111 that may be manufactured from a biocompatible material such as titanium, tantalum, stainless steel, plastic, ceramic, and/or the like. However, one or more components of the pump assembly 110 may also be located in separate housings that are appropriately coupled to each other. For example, the reservoir 114 could be attached to or placed within the housing 111, or it could be separated from the housing 111 and provided within a different housing that is connected to housing 111 via, e.g., a fluid coupling.

If provided in the pump assembly 110, the power supply 116 may be in the form of, e.g., a battery, capacitor, etc. The power supply 116 may preferably be connected to supply power to the pump mechanism 112, control electronics 118, pressure sensor 130, and any other components requiring electric power.

The control electronics 118 may be provided in any suitable form and may, for example, preferably include memory and a controller. The controller may be, e.g., an Application Specific Integrated Circuit (ASIC) state machine, a gate array, and/or may include a microprocessor. The control electronics 118 are preferably configured to operate the pump mechanism 112 (e.g., controlling infusion rate, etc.) and the pressure sensor 130. The control electronics 118 may also include components, etc. to operate other features not depicted in the exemplary system such as valves, temperature sensors, density sensors, alarms, etc.

The memory provided within the control electronics 118 may be used to store the pressure data collected using the pressure sensor 130. The pressure data may be stored and analyzed on-board within the control electronics 118 and/or using a remote device. The memory may be in any suitable format, e.g., flash memory devices, magnetic memory devices, optical data storage devices, etc.

The control electronics 118 may further include telemetry components configured to receive and/or send information after the pump assembly 110 and/or catheter 120 are implanted in a patient. Telemetry may also be used to transmit any data stored within the control electronics 118 of the infusion system relating to pressure, etc. as discussed herein. The pressure data may be transmitted to allow for analysis of the data, remote data storage (where, e.g., the amount of data may otherwise exceed the data storage capacity within the infusion system itself), etc.

Telemetry may also be used to, e.g., allow programming of the infusion rate, infusion times, selected pressure profiles, etc. Telemetry may further be used to provide information from the infusion device such as, e.g., the amount of fluid in the reservoir, etc. Such information may be used to determine whether the reservoir requires refilling, etc.

To detect pressure within the lumen 126 of catheter 120, pressure sensor 130 may be placed in contact with fluid in the lumen 126 of catheter 120 anywhere along the lumen 126 of the catheter 120 as long as the pressure sensor 130 is located proximal of the opening 128 (infusion section) of the catheter 120. It may, however, be preferred that the pressure sensor 130 be positioned outside of any location that would experience the same physiological pressure modulations as those expected at the selected internal delivery site where the infusion section of the catheter 120 is to be located. As depicted in FIG. 5, the pressure sensor 130 may preferably be contained within the housing 111 of the pump assembly 110 along with pump mechanism 112. The pressure sensor 130 may alternatively be located outside of the housing 111, although it may preferably be located close to the pump mechanism 112 such that leaks located between the pressure sensor 130 and the selected internal delivery site can potentially be detected.

The pressure sensor 130 may be adapted to read either gauge or absolute pressure of the fluid in the lumen 126 of the catheter 120. Because the methods of the present invention rely on comparison of pressure modulation profiles, changes in ambient pressure may be of limited importance in implementing the present invention because ambient pressure changes can typically be expected to exert the same influence on fluid in the lumen 126 as it does at the selected internal delivery site (e.g., on the CSF in the intrathecal space).

In those instances where, however, it is desirable to use pressure measurements from sensor 130 that are adjusted to account for ambient pressure outside of the catheter 120, a reference pressure may be detected within the patient's body in which catheter 120 is implanted or the reference pressure may be detected outside of patient's body. When detected within a patient's body, the reference pressure may be detected in any suitable location, e.g., proximate the pump assembly 110. The reference pressure may alternatively be obtained in any location capable of providing a pressure indicative of the external environment. Further discussions regarding reference pressures may be found in U.S. Patent Application Publication No. US 2005/0075624 A1, titled PRESSURE SENSING IN IMPLANTABLE MEDICAL DEVICES (Miesel).

In some methods and systems of the present invention, a reference pressure may be detected directly at the selected internal delivery site or at another location that would be expected to exhibit the same physiological pressure modulations expected at the selected internal delivery site (e.g., within the CSF in the intrathecal space using a separate pressure sensing system, etc.). In such a method/system, the reference pressure may also be used to detect physiological pressure modulations directly. Detecting physiological pressure modulations directly could potentially enhance detection of the presence or absence of corresponding pressure modulations within the fluid in the catheter lumen because the timing and frequency of the physiological pressure modulations at the selected internal delivery site would be known using the directly-measured reference pressure.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of identifying the presence of a catheter malfunction in an implanted catheter, the method comprising:
    measuring pressure of a fluid located within a lumen in a catheter implanted in a patient, wherein the lumen extends to an infusion section that is located at a selected internal delivery site in the cerebrospinal fluid of the patient;
    developing a pressure modulation profile of the cerebrospinal fluid of the patient based on the measured pressure of the fluid in the lumen, wherein developing the pressure modulation profile is based on measuring the pressure of the fluid in the lumen when the fluid is stationary within the lumen;
    comparing the pressure modulation profile to a selected pressure profile, wherein the selected pressure profile includes a physiological pressure modulation; and
    determining the existence of a catheter malfunction if the pressure modulation profile does not include a feature of the physiological pressure modulation of the selected pressure profile.

2. A method according to claim 1, further comprising providing an alert to the patient and/or a third party after determining the existence of the catheter malfunction.

3. A method according to claim 1, further comprising terminating delivery of the fluid to the lumen after determining the existence of a catheter malfunction.

4. A method according to claim 1, wherein the selected pressure profile is based at least in part on patient respiration.

5. A method according to claim 1, wherein the selected pressure profile is based at least in part on patient cardiac activity.

6. A method according to claim 1, wherein the selected internal delivery site is in the intrathecal space of the patient.

7. A method according to claim 6, wherein the selected pressure profile is based at least in part on changes in the pressure of the fluid as the patient moves between supine and upright postures.

8. A method according to claim 1, wherein the pressure modulation profile is developed based on pressure measurements obtained at only selected intervals.

9. A method according to claim 8, wherein the selected intervals are chosen based at least in part on the patient's circadian rhythm.

10. A method according to claim 1, wherein the fluid in the lumen of the catheter comprises a therapeutic substance, and wherein the method further comprises delivering the therapeutic substance to the patient through the infusion section of the catheter.

11. A method according to claim 1, further comprising storing data representative of the pressure modulation profile in a data storage device before comparing the pressure modulation profile to a selected pressure profile.

12. A method of identifying the presence of a catheter malfunction in an implanted catheter, the method comprising:
    measuring fluid pressure of a fluid located within a lumen in a catheter implanted in a patient, wherein the lumen extends to an infusion section that is located at a selected internal delivery site in the patient, wherein the selected internal delivery site is in the intrathecal space of the patient;
    developing a pressure modulation profile based on the measured fluid pressure of the fluid in the lumen;
    determining if the pressure modulation profile includes pressure modulation caused by patient cardiac activity by determining if the pressure modulation profile comprises a peak corresponding to the patient's cardiac activity; and
    determining that a catheter complication exists if the pressure modulation profile does not include the pressure modulation caused by the patient cardiac activity.

13. A method according to claim 12, wherein developing the pressure modulation profile is based on measuring the pressure of the fluid in the lumen when the fluid is stationary within the lumen.

14. A method according to claim 12, further comprising determining the existence of a catheter malfunction if the pressure modulation profile does not include pressure modulation caused by patient cardiac activity.

15. A method according to claim 14, further comprising providing an alert to the patient and/or a third party after determining the existence of the catheter malfunction.

16. A method according to claim 14, wherein the fluid comprises a therapeutic substance, and wherein the method further comprises:
    delivering the therapeutic substance to the patient through the infusion section of the catheter; and terminating delivery of the therapeutic substance to the patient after determining the existence of a catheter malfunction.

17. A method according to claim 12, wherein the pressure modulation profile is developed based on pressure measurements obtained at only selected intervals.

18. A method according to claim 17, wherein the selected intervals are chosen based at least in part on the patient's circadian rhythm.

19. A method of identifying the presence of a catheter malfunction in an implanted catheter, the method comprising:
   measuring fluid pressure of a fluid located within a lumen in a catheter implanted in a patient, wherein the lumen extends to an infusion section that is located at a selected internal delivery site in the patient, wherein the selected internal delivery site is in the intrathecal space of the patient;
   developing a pressure modulation profile based on the measured fluid pressure of the fluid in the lumen;
   determining if the pressure modulation profile includes pressure modulation caused by patient respiration by determining if the pressure modulation profile comprises a peak corresponding to the patient's respiratory activity; and
   determining that a catheter complication exists if the pressure modulation profile does not include the pressure modulation caused by the patient respiration.

20. A method according to claim 19, wherein developing the pressure modulation profile is based on measuring the pressure of the fluid in the lumen when the fluid is stationary within the lumen.

21. A method according to claim 19, further comprising determining the existence of a catheter malfunction if the pressure modulation profile does not include pressure modulation caused by patient respiration.

22. A method according to claim 21, further comprising providing an alert to the patient and/or a third party after determining the existence of the catheter malfunction.

23. A method according to claim 21, wherein the fluid comprises a therapeutic substance, and wherein the method further comprises:
   delivering the therapeutic substance to the patient through the infusion section of the catheter; and
   terminating delivery of the therapeutic substance to the patient after determining the existence of a catheter malfunction.

24. A method according to claim 19, wherein the pressure modulation profile is developed based on pressure measurements obtained at only selected intervals.

25. A method according to claim 24, wherein the selected intervals are chosen based at least in part on the patient's circadian rhythm.

26. An implantable infusion system comprising:
   a pump mechanism fluidly coupled to a reservoir to receive fluid contained within the reservoir;
   a catheter comprising a delivery lumen fluidly coupled to the pump mechanism, wherein the delivery lumen extends to an implantable infusion section in the catheter;
   a pressure sensor positioned to monitor fluid pressure within the delivery lumen of the catheter and provide a pressure signal representative of the fluid pressure; and
   control electronics connected to receive the pressure signal from the pressure sensor, wherein the control electronics further:
      develop a pressure modulation profile based on the fluid pressure measured in the delivery lumen;
      determine if the pressure modulation profile includes a physiological pressure modulation caused by movement between supine and upright postures; and
      determine that a catheter complication exists if the pressure modulation profile does not include the physiological pressure modulation caused by movement between supine and upright postures.

27. A system according to claim 26, wherein the pump mechanism, the reservoir, and the control electronics are contained within one or more implantable housings along with a power source.

28. An implantable infusion system comprising:
   a pump mechanism fluidly coupled to a reservoir to receive fluid contained within the reservoir;
   a catheter comprising a delivery lumen fluidly coupled to the pump mechanism, wherein the delivery lumen extends to an implantable infusion section in the catheter;
   a pressure sensor positioned to monitor fluid pressure within the delivery lumen of the catheter and provide a pressure signal representative of the fluid pressure; and
   control electronics connected to receive the pressure signal from the pressure sensor, wherein the control electronics further:
      develop a pressure modulation profile based on the fluid pressure measured in the delivery lumen;
      determine if the pressure modulation profile includes a pressure modulation caused by patient cardiac activity by determining if the pressure modulation profile comprises a peak corresponding to the patient's cardiac activity; and
      determine that a catheter complication exists if the pressure modulation profile does not include the peak corresponding to modulations caused by the patient cardiac activity.

29. A system according to claim 28, wherein the pump mechanism, the reservoir, and the control electronics are contained within one or more implantable housings along with a power source.

30. An implantable infusion system comprising:
   a pump mechanism fluidly coupled to a reservoir to receive fluid contained within the reservoir;
   a catheter comprising a delivery lumen fluidly coupled to the pump mechanism, wherein the delivery lumen extends to an implantable infusion section in the catheter;
   a pressure sensor positioned to monitor fluid pressure within the delivery lumen of the catheter and provide a pressure signal representative of the fluid pressure; and
   control electronics connected to receive the pressure signal from the pressure sensor, wherein the control electronics further:
      develop a pressure modulation profile based on the fluid pressure measured in the delivery lumen;
      determine if the pressure modulation profile includes pressure modulation caused by patient respiration by determining if the pressure modulation profile comprises a peak corresponding to the patient's respiratory activity; and
      determine that a catheter complication exists if the pressure modulation profile does not include the peak corresponding to the patient's respiratory activity.

31. A system according to claim 30, wherein the pump mechanism, the reservoir, and the control electronics are contained within one or more implantable housings along with a power source.

32. A method according to claim 1, wherein the selected pressure profile comprises a peak corresponding to the patient's cardiac activity.

33. A method according to claim 1, wherein the selected pressure profile comprises a peak corresponding to the patient's respiratory activity.

34. A method according to claim 1, wherein the selected pressure profile comprises a peak corresponding to the patient's cardiac activity and a peak corresponding to the patient's respiratory activity.

35. A method according to claim 12, wherein the method further includes determining if the pressure modulation profile includes pressure modulation caused by patient respiration by determining if the pressure modulation profile comprises a peak corresponding to the patient's respiratory activity.

* * * * *